(12) United States Patent
Alberto et al.

(10) Patent No.: US 7,053,242 B1
(45) Date of Patent: May 30, 2006

(54) CARBON MONOXIDE SOURCE FOR PREPARATION OF TRANSITION-METAL-CARBONYL-COMPLEXES

(75) Inventors: Roger Alberto, Winterthur (CH); Roger Schibli, Baden (CH)

(73) Assignee: Mallinckrodt Inc., St. Louis, MO (US)

( * ) Notice: Subject to any disclaimer, the term of this patent is extended or adjusted under 35 U.S.C. 154(b) by 681 days.

(21) Appl. No.: 10/089,036

(22) PCT Filed: Oct. 5, 2000

(86) PCT No.: PCT/EP00/09856

§ 371 (c)(1),
(2), (4) Date: Mar. 25, 2002

(87) PCT Pub. No.: WO01/25243

PCT Pub. Date: Apr. 12, 2001

(30) Foreign Application Priority Data

Oct. 5, 1999 (EP) .................................. 99203254

(51) Int. Cl.
*C07F 5/02* (2006.01)

(52) U.S. Cl. ..................................................... 562/882
(58) Field of Classification Search ............... 560/129; 568/1; 562/882
See application file for complete search history.

(56) References Cited

OTHER PUBLICATIONS

Bommer, An investigation of the Coordinating Properties of the Boranocarbonates and Tetrahydroborate, Diss. Abstr. Int. B 1978, 38(8), 3687.*
Malone, Leo J. and Manley, M.R.; "The Hydrolysis of Carbon Monoxide Borane"; Inorganic Chemistry; 1967; pp. 2260-2262; vol. 6(12).
Malone, Leo J. and Parry, R.W.; "Preparation and Properties of the boranocarbonates"; Inorganic Chemistry; 1967; pp. 817-822; vol. 6(4).
Mayer, Erwin; "Äther als Katalysatoren für die Reaktion von Diboran mit Lewis-Basen . . . "; Monatshefte für Chemie; 1971; pp. 940-945; vol. 102.

* cited by examiner

*Primary Examiner*—Paul A. Zucker

(57) ABSTRACT

The present invention relates to compounds that have a novel use as a carbon monoxide source and optionally as a reducing agent in the preparation of transition metal carbonyl complexes. The compounds are in general compounds of formula (I) wherein $X_1$, $X_2$ and $X_3$ are the same or different and either a Lewis base or hydride and Y is a sigma donating group. The invention furthermore relates to a method for the preparation of borane carbonate and to the use of $H_3BCO$ as a reducing agent.

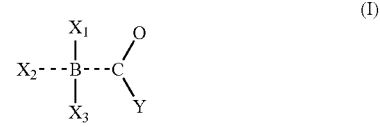

(I)

25 Claims, No Drawings

CARBON MONOXIDE SOURCE FOR PREPARATION OF TRANSITION-METAL-CARBONYL-COMPLEXES

The present invention relates to compounds that have a novel use as a carbon monoxide source and optionally as a reducing agent in the preparation of transition metal carbonyl complexes.

Carbonyl complexes are compounds that contain carbon monoxide as a coordinated ligand. Carbon monoxide is a common ligand in transition metal chemistry, in part due to the synergistic nature of its bonding to transition metals.

The bonding of CO to a metal consists of two components. The first component of the bonding is based on σ-donation, the overlap of a lone pair on the carbon atom with an empty d-orbital of the metal. The second component consists in π-back-donation from a filled d-orbital of the metal into an empty π* orbital of the carbon atom of CO. This second component is called pi-backbonding or pi-backdonation.

The above described formation of carbonyl complexes with transition metals is crucial for the application of such compounds in the labeling of proteins, peptides and a variety of other compounds. For many applications these molecules are labeled by means of a so-called labeling kit which contains the necessary reagents. Current kits are based on boron hydride as the reducing agent, further contain tartrate, lactose and borate buffer, pH 11.5, and are filled with gaseous CO as the CO source. The disadvantages of these known reaction mixtures are the slow dissolution of CO into the reaction solvent resulting in a decreased yield of carbonyl complexes, the impossibility of industrial preparation of large amounts of CO filled kit vials and the slow diffusion of CO even through tightly closed vials. Moreover, the pH is rather high, which is not convenient.

It is the object of the present invention to provide an alternative for CO and sodium boron hydride that does not have the above stated drawbacks.

It has now been found that compounds of formula I

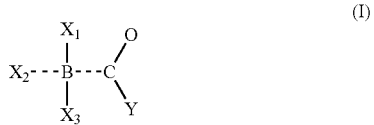

(I)

wherein:
$X_1$ is —H;
$X_3$ and $X_2$ are substituents which may be the same or different and are selected from the group consisting of —H, —$NH_xR_y$ with x+y=3, or —R, wherein R is a substituent which is bound by a carbon atom to the nitrogen or boron, respectively, and is preferably alkyl or aryl;
Y is —OH, —$OH_2$, —OR or —NHR, wherein R is a substituent which is bound by a carbon atom to the nitrogen or oxygen, respectively, and is preferably alkyl or aryl; or salts thereof can be used as a carbon monoxide (CO) source and optionally also as a reducing agent in the preparation of metal carbonyl complexes in aqueous solution. If Y is —OH or —$OH_2$, the compounds are acids which can be deprotonated (i.e. with NaOH). In that case, the compounds which are isolated are the salts (borano carbonate anion $R_3B$—$COO^{2-}$ plus the corresponding cation, e.g. $Li^+$, $Na^+$, $Ca^{2+}$, $Mg^{2+}$ and others). The reducing agent function is only present if at least one of $X_1$, $X_2$ and $X_3$ is a hydrogen. For stability reasons it is preferred that two of $X_1$, $X_2$ and $X_3$ are —H. The carbon monoxide is released upon heating an aqueous solution of the compound.

The advantages of the above compounds are the following. CO is produced for the first time in aqueous media under controllable conditions (pH, temperature) Carbonyl complexes of the claimed metals can be prepared in water at well defined conditions instead of organic solvents or under high pressure and high temperature. The Co source and reducing agent can be present in the same single compound, which is convenient since reduction is practically always required for the preparation of carbonyls. In case the metal to be complexed is Tc-99m or Re-188/186 kits can be produced without the demand of filling a vial with toxic and volatile CO. A major advantageous embodiment is a molecule combining the different functionalities in one compound. Such compound can act as a reducing agent and as an in situ CO source, where the CO is only produced if a protic solvent (like water) or a Lewis acid is present.

By varying the substituents at the different positions various types of compounds can be obtained. These can be subdivided in the following groups:

1. a borane carbonate compound in which $X_1$, $X_2$ and $X_3$ are —H and Y is —$OH_2$, and/or the corresponding salts of the mono- or dideprotonated borane carbonate $[H_3BCO_2]^{2-}$;
2. a borane amino acid (ammonia carboxy borane) in which $X_1$ is $NH_3$, $X_2$ and $X_3$ are —H and Y is —OH, and/or the corresponding salts of the monodeprotonated ammine borane carbonate $[(NH_3)H_2BCO_2]^-$;
3. alkylated borane amino acids (trialkyl ammonia carboxy boranes) in which $X_1$ is —$NH_xR_y$ with x+y=3, wherein R is a substituent which is bound by a carbon atom to the nitrogen and is preferably alkyl or aryl, $X_2$ and $X_3$ are —H and Y is —OH.
4. compounds of formula I wherein $X_1$ is an organic substituent bound by a carbon atom to boron, $X_2$ and $X_3$ are —H and Y is —$OH_2$.
5. compounds of formula I wherein $X_1$ and $X_2$ are organic substituents bound by a carbon atom to boron, $X_3$ is —H and Y is —$OH_2$.
6. borane carboxylic acid alkylester compounds wherein $X_1$, $X_2$ and $X_3$ are as defined under 1–5 above and Y is OR', in which R' is a substituent bound by a carbon atom to the oxygen, such as an alkyl, more in particular methyl or ethyl.
7. borane carbamate compounds wherein $X_1$, $X_2$ and $X_3$ are as defined in 1–5 above and Y is $NH_2$, NHR" or $NR"_2$, wherein R" is a substituent bound by a carbon atom to nitrogen, such as an alkyl, more in particular methyl or ethyl.

Particular examples of these compounds are:
boranocarbonate derivatives: [$H_3B$—$COOH_2$], [$H_3B$—COOH]M, [$H_2B$—$COO]M_2$, Na[$H_3B$—$COOCH_3$], wherein M is an alkali cation;
boranocarbamates: Na[$H_3BCONHCH_3$], M[$H_3B$—$CONH_2$], wherein M is an alkali cation;
ammine-boranocarbonates: [$H_3N$—$BH_2$—COOH], [$H_3N$—$BH_2$—COO]Li, [$(CH_3)_3N$—$BH_2$—COOH], [$(CH_3)H_2N$—$BH_2$—COOH], [$(CH_3)H_2N$—$BH_2$—COO]Li, [$(CH_3) H_2N$—$BH_2$—$COOCH_3$];
ammine-boranocarbamates: [$H_3N$—$BH_2$—$CONH_2$], [$(CH_3)_2HN$—$BH_2$—$CONHC_2H_5$]

The compounds of the invention can be prepared by means of or analogous to the methods as described by Burg et al., J. Am. Chem. Soc. 59, 780 (1937) for $BH_3CO$; Malone et al., Inorg. Chem. 6, 817 (1967) for $M_2[H_3B-COO]$ and $M[H_3B-COOC_2H_5]$; Howe et al., Inorg. Chem. 10, 930 (1971) for $M[H_3B-CONH_2]$; Spielvogel et al., J. Am. Chem. Soc. 102, 6343 (1980) for $[H_3N-BH_2-COOH]$ and $[(CH_3)_3N-BH_2-CONHC_2H_5]$; Spielvogel et al., Inorg. Chem. 23, 4322 (1984) for $[(CH_3)H_2N-BH_2-COOCH_3]$; Spielvogel et al., Inorg. Chem. 23, 1776 (1984) and J. Am. Chem. Soc. 98, 5702 (1976) for $[H_3N-BH_2-CONH_2]$, $[(CH_3)_2HN-BH_2-CONHC_2H_5]$.

The invention further relates to a method for preparing transition metal carbonyl complexes, wherein one or more of the compounds defined above are used as the CO source and optionally as the reducing agent. This method comprises in summary the release of CO from any compound of the invention, in particular from one or more of the compounds 1–7, in water or buffer due to protolysis and subsequent hydrolytic reactions. Concomitantly, the metal with which a carbonyl should be formed is reduced by the hydride substituent attached to boron. The compounds of the invention, in particular compounds 1–7, are dissolved in water or buffer and the metal is added either as a solid or as a solution. Protonation and hydrolysis of the compounds of the invention, in particular of compounds 1–7, releases CO. At the same time, the hydrides attached to the boron (—H) will reduce the metal center to a valency where the metal is able to coordinate the released CO. In that moment, carbonyl complexes are formed. The method according to the invention for preparing carbonyl complexes, thus comprises mixing the borano compounds of the invention with an aqueous solution of the metal in the form of a metal-ion or (per) metallate. "Metal" as used in this application is intended to encompass all forms of the metal, i.e. also metal ions and (per)metallates.

The compounds and method of the invention are suitable for the formation of any carbonyl complex, but in particular those in which the transition metal in the transition metal carbonyl complex is selected from the groups V-B to VIII-B metals. More in particular the method is suitable for preparing carbonyl complexes of the following transition metals: Vanadium (V), Chromium (Cr), Molybdenum (Mo), Tungsten (W), Manganese (Mn), Technetium (Tc), Rhenium (Re), Iron (Fe), Ruthenium (Ru), Osmium (Os), Cobalt (Co), Rhodium (Rh), Iridium (Ir) and Nickel (Ni) and their radioactive isotopes.

Furthermore, the invention provides a kit for preparing transition metal carbonyl complexes, comprising a compound according to the invention in aqueous solution, a stabilizing agent like tartrate, glucoheptonate, lactate, citrate and a buffer system like borate or phosphate. In a preferred embodiment thereof, the kit of the invention contains at least 2 mg borane carbonate, preferably in a borate buffer (pH 9.1) in an oxygen-free environment under a nitrogen atmosphere. It is preferred that the total volume of the solution after addition of the radioactive metal solution does not exceed 1 ml. However, larger volumes such as 2 or 3 ml may also be useful in certain circumstances. Suitable incubation conditions comprise heating the solution for about 20 minutes to 75° C.

The compounds of the invention can furthermore be used in water for the reduction of organic compounds with a selectivity and reactivity comparable to boron hydride or cyanoboronhydride.

In addition, it was found that $H_3BCO$ can be prepared continuously from $H_3B.THF$ and reacted in situ with an alcoholic solution of potassium hydroxide to give $K_2[H_3BCO_2]$. The key to the preparation is the control of the equilibrium between $H_3BCO$ and $H_3B.THF$: THF is selectively condensed from the gas stream at −50° C., while $H_3BCO$ (b.p. −64° C.) passes on, carried by a stream of carbon monoxide. Subsequently, this gas mixture is directly bubbled through an ethanolic solution of KOH at −78° C. Nucleophilic attack of $[OH^−]$ at the highly electrophilic carbon in $H_3BCO$ leads to the formation of $K_2[H_3BCO_2]$ in high yield. If required $H_3BCO$ itself can be isolated in a cold trap at −78° C. This method of preparing $H_3BCO$ is simpler and more convenient than the high pressure or ether-catalyzed procedures and can be scaled up to quantities of several grams or larger.

Thus, the invention relates to method for the preparation of borano carbonate, comprising the steps of:
a) reacting $BH_3.THF$ or a similar adduct in THF or a mixture of THF and another organic aprotic solvent with CO to generate $H_3BCO$;
b) passing the $H_3BCO$ thus generated through a cold solution of a hydroxide with a mono or dikationic counter ion and an aliphatic alcohol; and
c) after a suitable reaction time heating the alcoholic solution to precipitate the borano carbonate. The similar adduct is for example $H_3B(Et_2O)$. The hydroxide is for example selected from the group consisting of potassium hydroxide, sodium hydroxide or tetraalkyl ammonium hydroxide. The aliphatic alcohol can be selected from the group consisting of methanol, ethanol and isopropanol.

The compound $H_3BCO$ is also part of this invention. It has reducing properties and can be used for that purpose for example in the preparation of carbonyl complexes without high pressure CO as described above but then in aprotic or only weakly protic solvents. It is also possible to use $H_3BCO$ in situ while it is produced when CO is bubbled through THF solutions of "metals", such as for the synthesis of the macroscopic $[TcCl_3(CO)_3]_2$ or Re analogue.

The use of the compounds according to the invention is more broadly applicable than solely for the preparation of carbonyl complexes, but can also be applied in other circumstances wherein a CO source in aqueous solution is required. The invention also relates to the use of borano carbonate or derivatives thereof as a reducing agent for organic substrates, such as esters, imines or aldehydes, in water. The reducing power of these compounds is comparable to $BH_4-$ or cyanoborohydride and they can thus be a substitute for e.g. cyanoborohydride in bulk industrial processes.

The present invention is further illustrated in the following examples, that are given for illustration purposes only.

EXAMPLES

Example 1

Preparation of $K_2H_3BCO_2$

1. Synthesis of $BH_3.CO$ 4 g of $NaBH_4$ was carefully added to 15 ml of concentrated $H_3PO_4$ (dried overnight under high vacuum at room temperature) in vacuo (1 mbar) under vigorous stirring over a period of 2 hours. The evolving $BH_3$ was dried by passing it through a cool trap at −78° C. and was condensed in a second cool trap at −200° C. containing 70 ml of dry DME. The second trap was disconnected from the first trap and the vacuum line. The temperature was brought to −40° C.

Subsequently the trap was pressurized with 1.3 bar of dry CO. The reaction mixture was stirred in a cool bath at −40° C. (dry ice with acetonitrile) under 1.3 bar of CO overnight.

2. Synthesis of $K_2H_3BCO_3$

The gas outlet of the trap was connected to a 100 ml two-neck round-bottom flask (equipped with gas inlet and reflux condenser) containing 50 ml of dry ethanol and 3 g KOH. The cool bath of the trap was removed and the evolving $BH_3.CO$ was bubbled slowly through the ethanolic KOH solution at 0° C. The DME solution was slowly heated to 80° C. and the trap subsequently three times flushed with CO. After the evolution of $BH_3.CO$ had stopped the ethanolic solution was refluxed for 30 min. After cooling the solution to room temperature $K_2H_3BCO_2$ precipitated as a white powder which was filtered by a sintered glass filter, washed with ice cold ethanol and dried under vacuum.

Example 2

Labeling Experiment Using a Lyophilized Kit

A labeling kit was prepared by lyophilizing 1 mg $K_2[BH_3COO]$ in 0.1 ml of 0.1M PBS, pH 7.5 in a vial that was flushed with $N_2$. As an alternative a 0.1M borate buffer, pH 8.5 can be used.

For labeling, 1 ml of a generator eluted $[^{99m}TcO_4]^-$ saline solution is added. It was found that the yield is independent of the absolute amount of $[^{99m}TcO_4]^-$. The solution thus obtained is heated to 75° C. for 20 min.

The yields are between 80 and 100% for pH 7.5 and for pH 8.5.

To establish the identity of the compound, picolinic acid was added directly to the reaction solution, in which the carbonyl complex had been prepared. HPLC revealed the complex $[^{99m}Tc(OH_2)(pic)(CO)_3]$ by comparison with "cold" material, in the present case the same complex made with "cold" Rhenium. The "hot" material is found by means of a radioactivity detector, whereas the "cold" material is detected with a UV detector.

Example 3

Labeling Experiment with a So-Called "Wet Kit"

A vial containing 2 mg borane carbonate and a generator eluate of pertechnetate in borate buffer, pH 9.1, in a total volume of 1 ml was heated for 20 min. to 75° C. The labeling yield of the product $[^{99m}Tc(OH_2)(CO)_3]^+$ thus obtained was higher than 97%.

Example 4

Preparation of Potassium Hydrogen (carboxylato)-trihydroborate Starting from $H_3B.THF$ The apparatus used consisted of a 250 ml three-necked round-bottomed flask, connected to a cold-trap by a glass tube. The other two necks of the flask were sealed with rubber septa. A PTFE tube for the introduction of gas passed into the flask. From the outlet of the cold-trap, a PTFE tube passed into a 400 ml Schlenk tube. From the side-arm of the Schlenk tube passed a polytene tube leading to a silicone oil bubbler, which isolated the apparatus from the atmosphere.

The cold-trap and the Schlenk tube were immersed in Dewar flasks containing isopropanol. The apparatus was flushed with dry oxygen-free nitrogen for 30 minutes while the cold trap was cooled to −50° C. and the Schlenk tube to −78° C. by addition of dry ice to the respective Dewar flasks.

A solution of 5.0 g potassium hydroxide in 200 ml absolute ethanol was added to the Schlenk tube and allowed to cool to −78° C. The apparatus was briefly flushed with carbon monoxide, and 30 ml of a 1 moldm$^{-3}$ solution of borane-tetrahydrofuran complex in tetrahydrofuran was introduced into the round-bottomed flask. Carbon monoxide was bubbled into the solution so that approximately one bubble per second left the apparatus via the oil bubbler. The temperature of the middle cold-trap was maintained at between −45° C. and −55° C. by occasional addition of dry ice.

After two hours passage of carbon monoxide, 20 ml dimethoxyethane was introduced into the round-bottomed flask and an additional 20 ml dimethoxyethane was introduced into the middle cold-trap. Carbon monoxide was passed through the apparatus as before. After one hour, the Schlenk tube was disconnected from the rest of the apparatus, and allowed to warm to room temperature. The alcoholic solution was heated under reflux for 45 minutes. The resulting white precipitate was filtered off, washed with two 5 ml portions of absolute ethanol, and dried in vacuo to give 1.26 g product (43% based on $BH_3.THF$) as a white powder. Found K, 38.85% (gravimetric as $K_2Na[Co(NO_2)_6]$); $CH_4BKO_2$ requires K, 39.9%. $\delta_H$ (200 MHz, $D_2O$, 25° C.) 0.80 (1:1:1:1 quartet, $^1J(H-^{11}B)=80$ Hz; 1:1:1:1:1:1:1 septet, $^1J(H-^{10}B)=27$ Hz).

Example 5

Reduction of the Organic Substrate Sodium benzaldehyde-2-sulfonate with Boranocarbonate in Water Potassium boranocarbonate (100 mg) and sodium benzaldehyde-2-sulfonate (40 mg) were mixed in water (1 ml) and left to stand for 30 min at room temperature. Quantitative formation of sodium 2-(hydroxymethyl)-benzene sulfonate was confirmed by the disappearance of the $^1$H-NMR signal of the starting material at $\delta=10.77$, and the appearance of the product signal at $\delta=5.04$. The reaction mixture was odorless at the end of the experiment, indicating that the sulfonate group had not been reduced.

What is claimed is:

1. A method of using a compound, the method comprising:

preparing a transition metal carbonyl complex using a compound of the following formula as a CO source and as a reducing agent, wherein the using comprises:
releasing CO from the compound; and
reducing a metal, with which the transition metal carbonyl complex is to be formed, with a hydride substituent attached to boron (B), wherein:

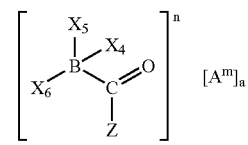

$X_4$ is —H;

$X_5$ and $X_6$ are substituents which are independently selected from the group consisting of —H, —$NH_xR_y$ and R, wherein x and y are integers and x+y=3, wherein R is bound by a carbon atom to the nitrogen or boron, respectively;

Z is —OH, —OH$_2$, —OR or —NHR, wherein R is a substituent that comprises a carbon atom and is bound by the carbon atom to the nitrogen or oxygen, respectively;

A is a cation selected from hydrogen and an alkali or alkaline earth metal;

n is 0, −1 or −2; and a and m are independently 0, +1 or +2.

2. The method as claimed in claim 1, wherein the transition metal in the transition metal carbonyl complex is selected from the groups V-B to VIII-B metals.

3. The method as claimed in claim 2, wherein the transition metal in the transition metal carbonyl complex is selected from the group consisting of Vanadium (V), Chromium (Cr), Molybdenum (Mo), Tungsten (W), Manganese (Mn), Technetium (Tc), Rhenium (Re), Iron (Fe), Ruthenium, (Ru), Osmium (Os), Cobalt (Co), Rhodium (Rh), Iridium (Ir) and Nickel (Ni).

4. A method for preparation of boranocarbonate, comprising:
   a) reacting BH$_3$-THF or an adduct thereof in THF or a mixture of THF and an organic aprotic solvent with CO to generate H$_3$BCO;
   b) passing the H$_3$BCO thus generated through a cold solution of a hydroxide with a mono or dicationic counter ion and a lower alkyl C$_{1-5}$ alcohol; and
   c) after a suitable reaction time, heating the alcoholic solution to precipitate the boranocarbonate.

5. The method of claim 4, wherein the adduct is H$_3$B (Et$_2$O).

6. The method of claim 4, wherein the hydroxide is selected from the group consisting of potassium hydroxide, sodium hydroxide and tetraalkyl ammonium hydroxide.

7. The method of claim 4, wherein the alcohol is selected from the group consisting of methanol, ethanol and isopropanol.

8. The method of claim 1, further comprising making a solution comprising the compound and a protic solvent.

9. The method of claim 8, further comprising heating the solution, wherein the heating of the solution comprises releasing carbon monoxide.

10. The method of claim 1, further comprising making a solution comprising the compound and a Lewis acid.

11. The method of claim 10, further comprising heating the solution, wherein the heating of the solution comprises releasing carbon monoxide.

12. The method of claim 1, further comprising making a solution comprising the compound and water.

13. The method of claim 12, further comprising heating the solution, wherein the heating of the solution comprises releasing carbon monoxide.

14. The method of claim 1, wherein n is −1 or −2, m is +1 or +2, and m+n is equal to zero.

15. The method of claim 1, wherein (a×m)+n is equal to zero.

16. The method of claim 1, wherein at least one of X$_5$ and X$_6$ is —H.

17. A method of using a compound, the method comprising:
   preparing a transition metal carbonyl complex using a compound of the following formula as a CO source and as a reducing agent, wherein the using comprises:
   releasing CO from the compound; and
   reducing a metal, with which the transition metal carbonyl complex is to be formed, with a hydride substituent attached to boron (B),

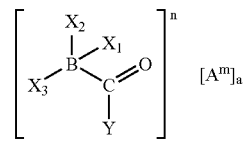

wherein:
X$_1$, X$_2$ and X$_3$ are the same or different and are selected from the group consisting of Lewis bases and hydrides;

Y is a sigma donating group;

A is a cation selected from the group consisting of hydrogen, alkali and alkaline earth metals;

n is 0, −1 or −2;

m is 0, +1 or +2; and a is 0, +1 or +2.

18. The method of claim 17, further comprising mixing the compound with a protic solvent or a Lewis acid.

19. The method of claim 17, further comprising making an aqueous solution comprising the compound.

20. The method of claim 17, wherein: (a×m)+n is equal to zero.

21. The method of claim 19, wherein the compound is:
a borane carbonate compound in which X$_1$, X$_2$ and X$_3$ are —H, and Y is —OH$_2$;

a corresponding salts of the mono- or dideprotonated borane carbonate [H$_3$BCO$_2$]$^{2-}$;

a borane amino acid in which X$_1$ is NH$_3$, X$_2$ and X$_3$ are —H, and Y is —OH; or a corresponding salt of the monodeprotonated ammine borane carbonate [(NH$_3$)H$_2$BCO$_2$]$^-$.

22. The method of claim 19, wherein the compound is an alkylated borane amino acid in which X$_1$ is —NH$_x$R$_y$ with x+y=3, wherein R is alkyl or aryl and is bound by a carbon atom to the nitrogen, X$_2$ and X$_3$ are —H, and Y is —OH.

23. The method of claim 19, wherein X$_1$ is an organic substituent bound by a carbon atom to boron, X$_2$ and X$_3$ are —H, and Y is —OH$_2$.

24. The method of claim 19, wherein the compound is selected from the group consisting of:
boranocarbonate derivatives selected from the group consisting of [H$_3$B—COOH$_2$], [H$_3$B—COOH]M, [H$_3$B—COO]M$_2$ and Na[H$_3$B—COOCH$_3$], wherein M is an alkali cation;

boranocarbonates selected from the group consisting of Na[H$_3$BCONHCH$_3$] and M[H$_3$B—CONH$_2$], wherein M is an alkali cation;

ammine-boranocarbonates selected from the group consisting of [H$_3$N—BH$_2$—COOH], [H$_3$N—BH$_2$—COO]Li, [(CH$_3$)$_3$N—BH$_2$—COOH], [(CH$_3$)H$_2$N—BH$_2$—COOH], [(CH$_3$)H$_2$N—BH$_2$—COO]Li and [(CH$_3$)H$_2$N—BH$_2$—COOCH$_3$]; and amine-boranocarbamates selected from the group consisting of [H$_3$N—BH$_2$—CONH$_2$] and [(CH$_3$)$_2$HN—BH$_2$—CONHC$_2$H$_5$].

25. The method of claim 1, wherein R is alkyl or aryl.

* * * * *